United States Patent
Sapiens et al.

(10) Patent No.: US 10,261,014 B2
(45) Date of Patent: Apr. 16, 2019

(54) NEAR FIELD METROLOGY

(71) Applicant: KLA-Tencor Corporation, Milpitas, CA (US)

(72) Inventors: Noam Sapiens, Bat Yam (IL); Joel Seligson, Misgav (IL); Vladimir Levinski, Migdal HaEmek (IL); Daniel Kandel, Aseret (IL); Yoel Feler, Haifa (IL); Barak Bringoltz, Rishon LeTzion (IL); Amnon Manassen, Haifa (IL); Eliav Benisty, Migdal Ha'emek (IL)

(73) Assignee: KLA-Tencor Corporation, Milpitas, CA (US)

( * ) Notice: Subject to any disclaimer, the term of this patent is extended or adjusted under 35 U.S.C. 154(b) by 0 days.

(21) Appl. No.: 14/583,447

(22) Filed: Dec. 26, 2014

(65) Prior Publication Data
US 2015/0198524 A1   Jul. 16, 2015

Related U.S. Application Data

(63) Continuation of application No. PCT/US2013/047682, filed on Jun. 25, 2013.
(Continued)

(51) Int. Cl.
*G01N 21/55* (2014.01)
*G01N 21/47* (2006.01)
(Continued)

(52) U.S. Cl.
CPC ......... *G01N 21/4788* (2013.01); *G02B 27/56* (2013.01); *G02B 27/58* (2013.01); *G01N 2201/06113* (2013.01)

(58) Field of Classification Search
CPC ....... F24J 2/08; F24J 2/06; G02B 3/00; G01N 21/4788; G01N 2201/06113
(Continued)

(56) References Cited

U.S. PATENT DOCUMENTS 752,894 A    2/1904  Fessenden
5,537,634 A *  7/1996  Fye ..................... H04J 14/0298
                                                        398/76
(Continued)

FOREIGN PATENT DOCUMENTS

JP    H08316125 A    11/1996
JP    H11353728 A    12/1999
(Continued)

OTHER PUBLICATIONS

Bass, M. et al., Handbook of Optics, Devices, Measurements & Properties, vol. II, 2nd Edition, McGraw-Hill 1995, p. 1.11.
(Continued)

*Primary Examiner* — Isiaka O Akanbi
(74) *Attorney, Agent, or Firm* — Suiter Swantz pc llo

(57) ABSTRACT

Metrology systems and methods are provided herein, which comprise an optical element that is positioned between an objective lens of the system and a target. The optical element is arranged to enhance evanescent modes of radiation reflected by the target. Various configurations are disclosed: the optical element may comprise a solid immersion lens, a combination of Moiré-elements and solid immersion optics, dielectric-metal-dielectric stacks of different designs, and resonating elements to amplify the evanescent modes of illuminating radiation. The metrology systems and methods are configurable to various metrology types, including imaging and scatterometry methods.

17 Claims, 9 Drawing Sheets

Related U.S. Application Data

(60) Provisional application No. 61/664,477, filed on Jun. 26, 2012.

(51) Int. Cl.
*G02B 27/56* (2006.01)
*G02B 27/58* (2006.01)

(58) Field of Classification Search
USPC .................. 356/445, 317; 359/390, 656, 626
See application file for complete search history.

(56) References Cited

U.S. PATENT DOCUMENTS

| | | | | |
|---|---|---|---|---|
| 5,627,668 | A * | 5/1997 | Fye | H04J 14/0298 398/152 |
| 5,715,039 | A * | 2/1998 | Fukuda | G03F 1/14 355/53 |
| 5,883,872 | A * | 3/1999 | Kino | G11B 7/1374 369/112.24 |
| 5,910,940 | A * | 6/1999 | Guerra | B82Y 10/00 369/112.24 |
| 6,091,694 | A * | 7/2000 | Spath | G02B 1/02 359/664 |
| 6,574,174 | B1 * | 6/2003 | Amble | G11B 7/0065 369/44.26 |
| 6,594,086 | B1 * | 7/2003 | Pakdaman | G02B 3/00 359/368 |
| 6,778,327 | B2 | 8/2004 | Pakdaman et al. | |
| 7,180,833 | B2 | 2/2007 | Takeda et al. | |
| 7,196,787 | B2 | 3/2007 | Uhl et al. | |
| 7,230,902 | B2 * | 6/2007 | Saito | G02B 27/283 369/110.02 |
| 7,317,824 | B2 | 1/2008 | Ghinovker et al. | |
| 7,385,758 | B2 | 6/2008 | Aono et al. | |
| 7,528,941 | B2 | 5/2009 | Kandel et al. | |
| 7,541,201 | B2 | 6/2009 | Ghinovker | |
| 7,616,313 | B2 | 11/2009 | Kandel et al. | |
| 7,656,528 | B2 | 2/2010 | Abdulhalim et al. | |
| 7,808,879 | B2 * | 10/2010 | Bell, Jr. | B82Y 10/00 369/112.23 |
| 7,894,308 | B2 * | 2/2011 | Peng | G11B 5/1278 360/59 |
| 8,209,767 | B1 | 6/2012 | Manassen | |
| 8,243,273 | B2 | 8/2012 | Levinski et al. | |
| 8,300,307 | B2 * | 10/2012 | Tschekalinskij | B82Y 20/00 359/368 |
| 2001/0050896 | A1 * | 12/2001 | Hajjar | B82Y 10/00 369/112.24 |
| 2003/0156280 | A1 | 8/2003 | Reinhorn et al. | |
| 2004/0062503 | A1 * | 4/2004 | Challener | B82Y 20/00 385/129 |
| 2006/0011862 | A1 * | 1/2006 | Bernstein | B01L 3/502715 250/461.2 |
| 2006/0033921 | A1 * | 2/2006 | Den Boef | G03F 7/70341 356/446 |
| 2006/0050283 | A1 * | 3/2006 | Hill | G03F 7/70633 356/512 |
| 2008/0217794 | A1 | 9/2008 | Smith et al. | |
| 2008/0304054 | A1 * | 12/2008 | Goosens | H01L 22/12 356/237.4 |
| 2010/0072353 | A1 | 3/2010 | Tschekalinskij et al. | |
| 2011/0063717 | A1 * | 3/2011 | Consonni | G01Q 60/22 359/298 |
| 2011/0073775 | A1 * | 3/2011 | Setija | G03F 7/70633 250/492.1 |
| 2011/0188032 | A1 | 8/2011 | Verma et al. | |
| 2012/0107738 | A1 * | 5/2012 | Argoitia | C09C 1/0015 430/110.3 |
| 2012/0307606 | A1 * | 12/2012 | Khizroev | G11B 5/64 369/13.33 |

FOREIGN PATENT DOCUMENTS

| | | |
|---|---|---|
| JP | 2001141941 A | 5/2001 |
| JP | 2001176112 A | 6/2001 |
| JP | 2005515514 A | 5/2005 |
| JP | 2008541042 A | 11/2008 |
| JP | 2009008690 A | 1/2009 |

OTHER PUBLICATIONS

Corle, T. R. et al., Confocal scanning optical microscopy and related imaging systems, Academic Press 1996, Sections 2.8.3 and 3.7.

Office Action dated Jun. 20, 2017 for Japanese Patent Appln. No. 2015-520408.

Office Action dated Feb. 3, 2017 for Taiwan Patent Appln. No. 102122771.

Alitalo, P. et al., "Near-field enhancement and subwavelength imaging in the optical region using a pair of two-dimensional arrays of metal nanospheres", Physical Review B, 74, 235425, dated Dec. 15, 2006, Abstract, 3 pages.

* cited by examiner

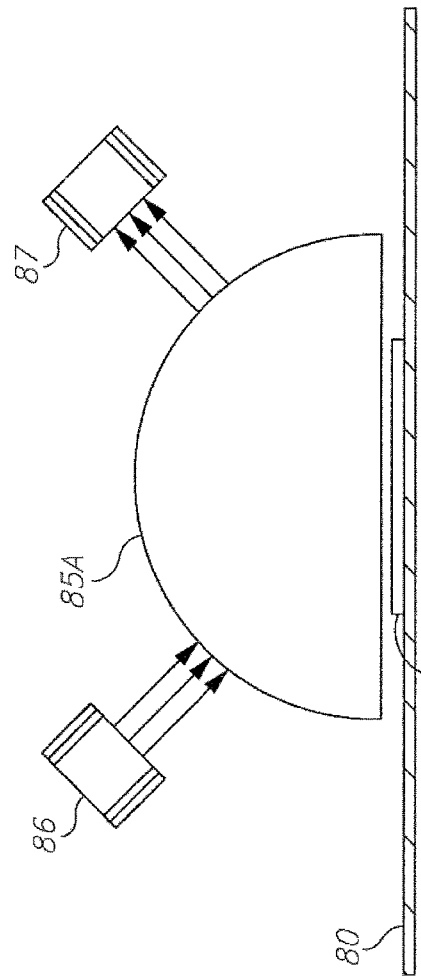
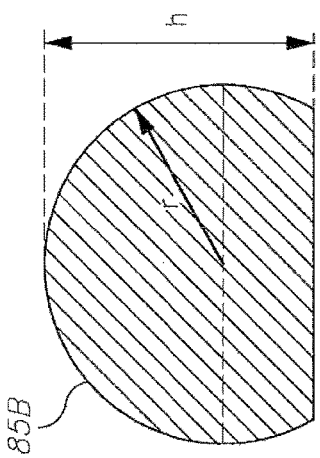
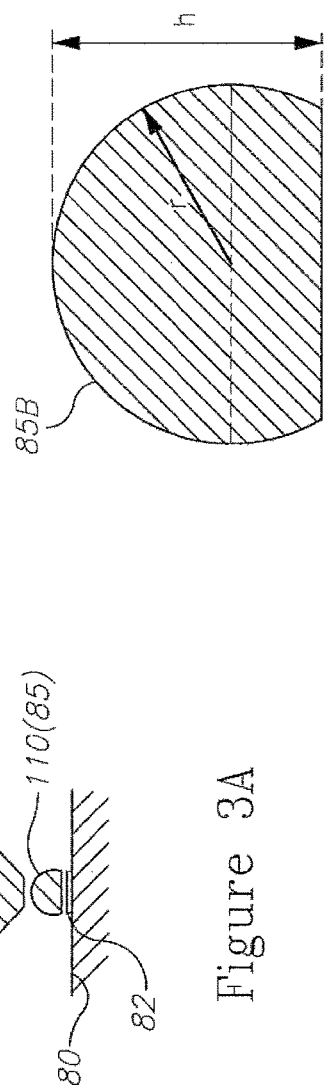
Figure 3B
Figure 3C
Figure 3A

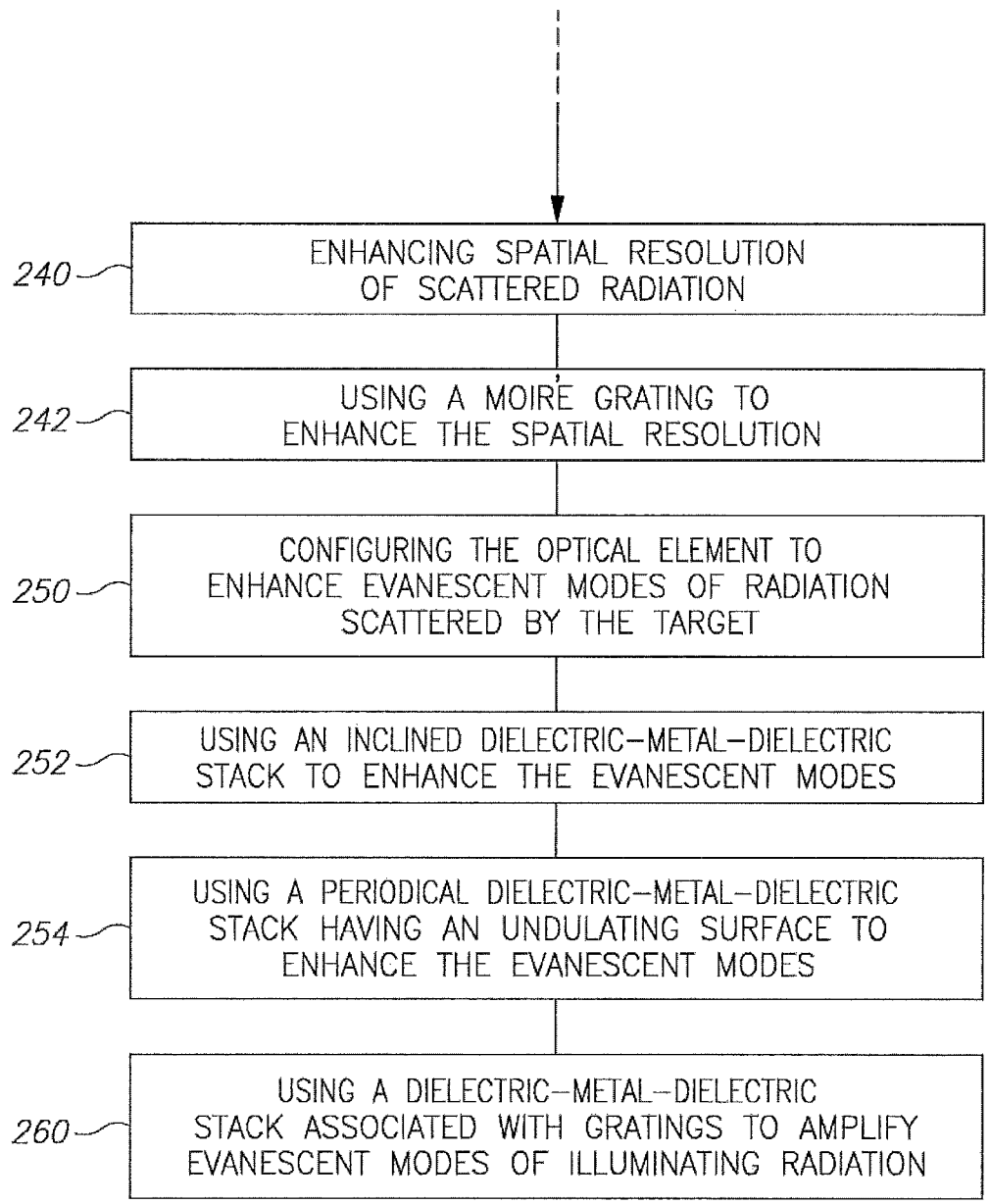
Figure 7 (cont. 1)

NEAR FIELD METROLOGY

CROSS-REFERENCE TO RELATED APPLICATIONS

This application is filed under 35 U.S.C. § 111(a) and § 365(c) as a continuation of International Patent Application No. PCT/US2013/047682, filed on Jun. 25, 2013, which application claims the benefit of U.S. Provisional Patent Application No. 61/664,477, filed on Jun. 26, 2012, which applications are incorporated herein by reference in their entireties.

TECHNICAL FIELD

The present invention relates to the field of metrology, and more particularly, to near field technologies in metrology.

BACKGROUND

The main measurement quantities for semiconductor metrology are overlay (OVL), critical dimensions (CD) (which includes: mean critical dimension, height and side wall angle; thus characterizing the printed features profile) and focus-dose. There are two main approaches for optical metrology available: imaging and scatterometry. Overlay can be measured using either approach while critical dimensions (performed on device rule targets) can only be performed using scatterometry methods. Imaging indicates a method where the required metrics are extracted from some visualization of a certain target. The visualization is achieved by measuring light intensity in an optically conjugate plane to the target plane. Scatterometry is in essence, extraction of said quantities from information achieved from discrete or continuous diffraction orders from the target. These diffraction orders are usually viewable in an optically conjugate plane of the system objective pupil. The electric field in this pupil contains a truncated Fourier transform of the target, the truncation depending on the numerical aperture (angular acceptance) of the said objective. The continuous reduction of the target sizes and overlay control budgets require increasingly accurate metrological methods.

Imaging technologies include, but are not limited to: classical imaging as disclosed e.g., by U.S. Pat. No. 7,541,201, which is incorporated herein by reference in its entirety, and order selected imaging as disclosed e.g., by U.S. Pat. No. 7,528,941, which is incorporated herein by reference in its entirety.

FIGS. 1A-1C are schematic illustration of contours of pupil light distribution for different target sizes, according to the prior art. FIGS. 1A-C illustrate a main disadvantage of typical imaging technologies, based on an example suggested by U.S. Pat. No. 7,528,941, referred to above. These optical configurations are characterized by quasi-normal illumination and zero order blocking in the collection pupil. The target image is constructed by interference of the ±1 diffraction orders. Such a configuration provides a robust (i.e., independent of optical imperfections) OVL measurement with very high performance. The system resolution is given by $P > \lambda/[NA \cdot (1+\sigma)]$, where $\lambda$ is the wavelength of light, NA is the system numerical aperture and $\sigma$ is a partial coherence factor. For example, in the visual spectrum with a standard NA=0.7 and $\sigma$=0.5, the pitch limit is P>400 nm. FIGS. 1A, 1B, and 1C illustrate the 1% of maximum intensity contours 75 in the pupil plane for a grating having a 1000 nm pitch and imaged with $\lambda$=532 nm, for target sizes 27 µm, 15 µm and 10 µm, respectively. Circles 71 indicate the 0.7NA pupil region and circles 72 indicate the zero order blocking obscuration. Evidently, targets smaller than 10 µm cannot be measured using this technology since the limited pupil NA leads to truncation of the transferred signal (any light out of the 0.7NA region is truncated). As a result of this truncation, significant image distortion is observed. Since the current market requirement for target size is 5 µm, this optical technology cannot be used without significant increase of the pupil's NA.

Imaging based OVL measurements are performed using a conventional microscope which provides a far-field image of the OVL target on a CCD. There are various imaging targets, as disclosed e.g., by U.S. Pat. No. 7,317,824, which is incorporated herein by reference in its entirety.

Scatterometry technologies include, but are not limited to: spectroscopic scatterometry, as disclosed e.g., by U.S. Pat. No. 7,616,313, which is incorporated herein by reference in its entirety, and angle-resolved scatterometry, as disclosed e.g. by U.S. Pat. No. 7,656,528, which is incorporated herein by reference in its entirety.

FIG. 4A illustrates typical dielectric-metal-dielectric stacks 90. In such an application, there is difficulty in dampening an amplitude enhancement by the interface between dielectric layers 90A, 90C and the surrounding air.

SUMMARY

The present invention generally comprises a metrology system having an optical element that is positioned between an objective lens and a target, the optical element arranged to enhance evanescent modes of radiation interacting with the target and the metrology system is arranged to measure at least a first diffraction order of radiation scattered by the target.

In example embodiments, the optical element is arranged to enhance evanescent modes of radiation reflected by the target and possibly also to convert evanescent modes of radiation interacting with the target to propagating modes. Various configurations are disclosed. In example embodiments, the optical element may comprise a solid immersion lens, a combination of Moiré-elements and solid immersion optics, dielectric-metal-dielectric stacks of different designs, and resonating elements. The metrology systems and methods are configurable to various metrology types, including imaging and scatterometry methods. Embodiments of the metrology systems and methods may be applied either as capturing devices or as illuminating devices.

A general object of the present invention is to provide systems and methods that enable metrology on device-like targets, or directly on devices with pitches well below 200 nm.

Another object of the present invention is to provide a robust evanescent mode enhancement, which enables detection of evanescent waves and thus imaging of sub resolved periodic structures. The robustness of the invention is expressed in that in embodiments, there is no strong dependency on the exact characteristics of the surrounding medium and structures.

These and other objects, advantages and features of the present invention will be better appreciated by those having ordinary skill in the art in view of the following detailed description of the invention in view of the drawings.

BRIEF DESCRIPTION OF THE DRAWINGS

For a better understanding of embodiments of the invention and to show how the same may be carried into effect, reference will now be made, purely by way of example, to the accompanying drawings in which like numerals designate corresponding elements or sections throughout.

In the accompanying drawings:

FIG. 3A is a high level schematic illustration of a metrology system having a solid immersion lens as an optical element, according to some embodiments of the invention;

FIG. 3B is a high level schematic illustration of a metrology system having a solid immersion lens as an optical element, according to some embodiments of the invention;

FIG. 3C is a high level schematic illustration of a metrology system having a solid immersion lens as an optical element, according to some embodiments of the invention;

DETAILED DESCRIPTION

Figure 1C:
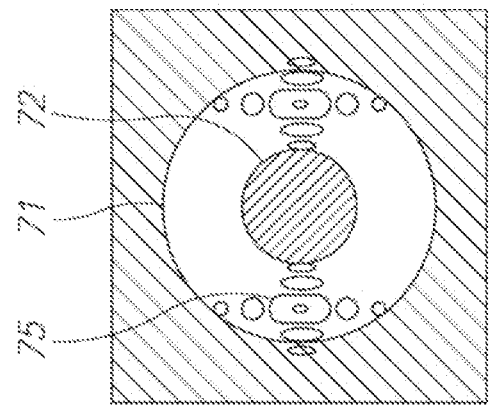
FIG. 1C is a schematic illustration of contours of pupil light distribution for a target size of 10 μm, according to the prior art.
Figure 1B:
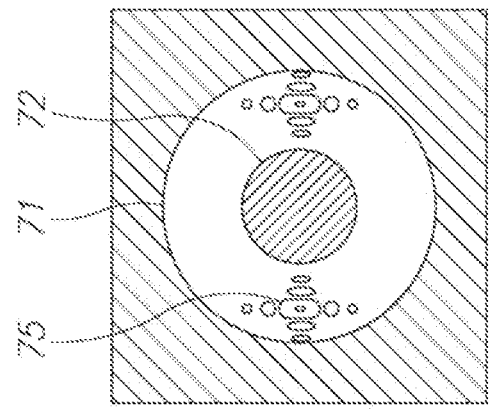
FIG. 1B is a schematic illustration of contours of pupil light distribution for a target size of 15 μm, according to the prior art.
Figure 1A:
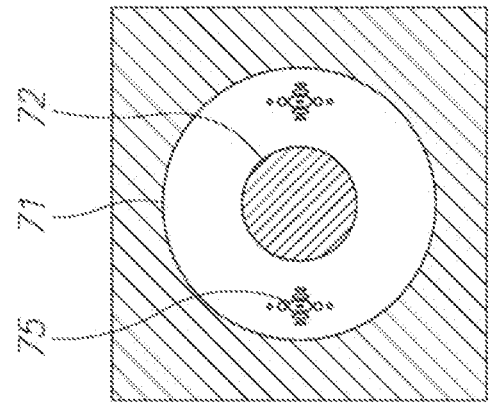
FIG. 1A is a schematic illustration of contours of pupil light distribution for a target size of 27 μm, according to the prior art.

At the outset, it should be appreciated that like drawing numbers on different drawing views identify identical, or functionally similar, structural elements of the invention. While the present invention is described with respect to what is presently considered to be the preferred aspects, it is to be understood that the invention as claimed is not limited to the disclosed aspect. Also, it is to be understood that the invention is not limited in its application to the details of construction and the arrangement of the components set forth in the following description or illustrated in the drawings. The invention is applicable to other embodiments or of being practiced or carried out in various ways and is intended to include various modifications and equivalent arrangements within the spirit and scope of the appended claims.

Furthermore, it is understood that this invention is not limited to the particular methodology, materials and modifications described and as such may, of course, vary. It is also understood that the terminology used herein is for the purpose of describing particular aspects only, and is not intended to limit the scope of the present invention, which is limited only by the appended claims.

Unless defined otherwise, all technical and scientific terms used herein have the same meaning as commonly understood to one of ordinary skill in the art to which this invention belongs. Although any methods, devices or materials similar or equivalent to those described herein can be used in the practice or testing of the invention, the preferred methods, devices, and materials are now described.

In the below description, an embodiment is an example or implementation of the invention. The various appearances of "one embodiment", "an embodiment", "certain embodiments" or "some embodiments" do not necessarily all refer to the same embodiments.

The terms "target" or "metrology target" as used herein in this application refers to any structure that is used for metrology needs. Targets may be part of any layer in the lithographic process, and targets may include different structures on the same layer or on different layers. In the present disclosure, metrology targets are exemplified, in a non-limiting manner, as grating based imaging targets. The grating examples simplify the explanation, but are not to be understood as limiting the disclosure.

The term "numerical aperture (NA)" as used herein in this application refers to the number used to characterize the range of angles over which the optical system can illuminate the target, for example, without wishing to be bound by theory, NA may be expressed as NA=n×sin α with α being the maximal illumination angle and n being the refractive index of the system (i.e., of the objective lens or of the optical elements inserted in the invention between the target and the objective lens).

The term "grating" as used herein in this application refers to any periodical element or feature.

Figure 2A:
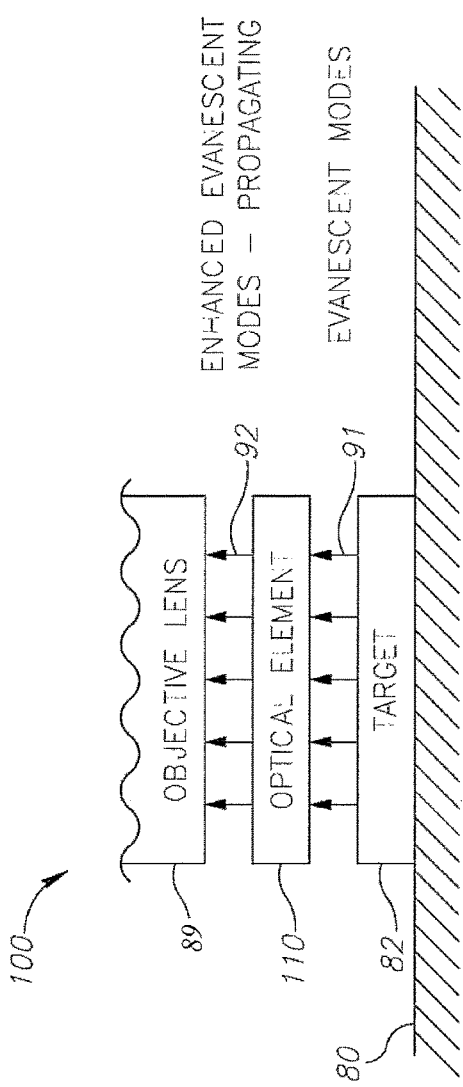
FIG. 2A is a high level schematic illustration of a metrology system according to some embodiments of the invention.
Figure 2B:
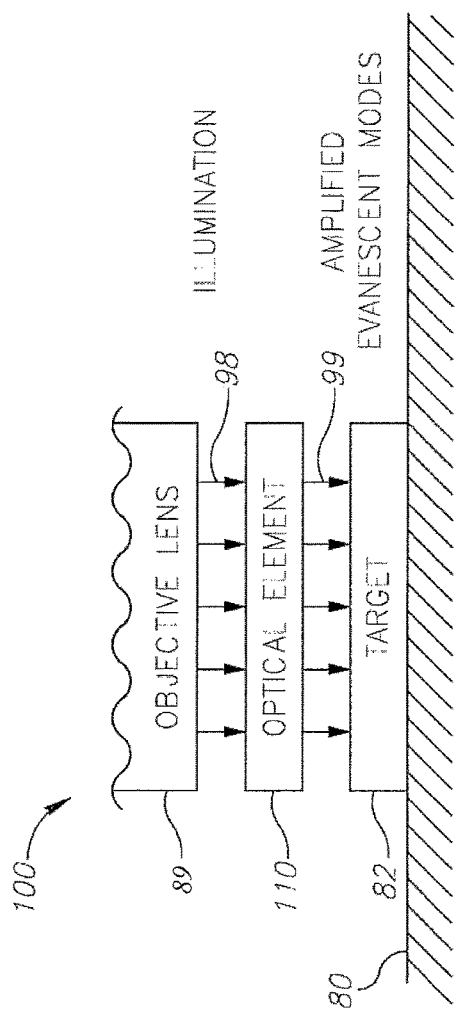
FIG. 2B is a high level schematic illustration of a metrology system according to some embodiments of the invention.

Referring now to the Figures, FIGS. 2A and 2B are high level schematic illustrations of metrology system 100 according to some embodiments of the invention. Metrology system 100 comprises optical element 110 positioned between objective lens 89 of system 100 (see also FIG. 3A) and target 82. Optical element 110 illustrated in FIG. 2A is arranged to enhance evanescent modes 91 of radiation reflected by target 82 in order to yield propagating modes 92 that carry at least some of the information of evanescent modes 91. In some example embodiments, optical element 110 may be designed to convert evanescent modes of radiation interacting with the target into propagating modes. Optical element 110 illustrated in FIG. 2B is arranged to amplify evanescent modes 99 of illumination 98 that is irradiated on target 82 in order to enhance the information content of the reflections, as explained in more detail below. Metrology system 100 applies near-field technologies to enhance the information content in the measures with information from evanescent modes 91 by making at least a part thereof into propagating modes.

In some example embodiments, metrology system 100 may be used both in imaging-based metrology as well as in scatterometry-based metrology. For example, metrology system 100 may be arranged to generate an image of target 82 that has enhanced resolution with respect to prior art systems.

Imaging-Based Overlay Metrology

In the following, reference is made in a non-limiting exemplary manner to grating targets. In such targets, there is at least one grating in each target layer. In order to get information about the grating position, at least two diffraction orders must be used, e.g., zero order and one of the first diffraction orders. This limits the grating pitch to the system resolution, given by $P>\lambda/[NA\cdot(1+\sigma)]$, where $\lambda$ is the wavelength of light, NA is the system numerical aperture and $\sigma$ is a partial coherence factor. For example, in the visual spectrum with a standard NA=0.7 and $\sigma$=0.5, the pitch limit is P>400 nm. In actual wafer measurements, targets with pitches P>800 nm are used. Furthermore, the resolution limit defines the minimal target size and the overall performance of an OVL measurement. The latter is directly related to the number of periods that can be printed in an OVL target of a given size.

In reference to FIGS. 2A, 2B, and 3A-3C, metrology system 100 may be arranged to measure at least a first diffraction order of radiation scattered by targets 82 which may be smaller than 10 nm (again, targets smaller than 10 µm cannot be measured using common technology as is discussed above in the Background). In some example embodiments, optical element 110 comprises solid immersion lens 85 arranged to enhance a resolution of metrology system 100 to make such target measurements possible.

Scatterometry-Based Overlay (OVL) and Critical Dimension (CD) Metrology

The effect of a limited NA on scatterometry technologies is twofold: The sensitivity of the measured signal to the output parameters (OVL, CD) is pupil location dependent. As may be shown in simulations, an increase of pupil NA by a factor of 2-3 causes an increase in the sensitivity by a factor of 4-5. This improves performance (accuracy, precision etc.) accordingly, by the same factor. Furthermore, the target size is primarily defined by the illumination spot size. The spot size, for a given illumination spectrum, is inversely proportional to the illumination NA. Accordingly, an increase of the illumination NA by a factor of 2-3 allows for a target size reduction by the same factor.

Embodiments of system 100 which relate to two main types for scatterometry based OVL measurement, namely spectroscopic scatterometry and angle-resolved scatterometry, are discussed below in a non-limiting manner. In both aspects, system 100 exhibits improved performance, among others due to using a higher NA.

FIGS. 3A-3C are high level schematic illustrations of metrology system 100 having solid immersion lens 85 as optical element 110, according to some embodiments of the present invention. FIG. 3A is a high level schematic illustration of system 100 and FIG. 3B is an illustration of using system 100 for spectroscopic scatterometry (discussed below). In an example embodiment, optical element 110 may be hemispherical solid immersion lens 85A as is shown in FIGS. 3A and 3B. In an example embodiment, optical element 110 may be hyper-hemispherical lens 85B (so-called Amici-lens or Weierstrass-lens) as is shown in FIG. 3C.

Metrology system 100 may comprise microscope illumination arm 86 directed through beam splitter 88 to objective lens 89, and microscope collection arm 87 receiving radiation reflected from target 82 through objective lens 89 and beam splitter 88.

System 100 uses solid immersion lenses (SIL) 85 not only to increase the NA, but also, generally, to enable propagation of evanescent waves. The transformation of evanescent waves to propagating waves increases the information content available to system 100 from target 82 (see FIG. 2A). For example, embodiments of solid immersion optical element 85 may comprise aplanatic lenses such as hemispherical lens 85A in FIG. 3B or hyper-hemispherical lens 85B in FIG. 3C. Lens 85 may be situated with its flat surface towards target 82, with the separation between the flat surface of lens 85 and target 82 being much less than the wavelength of light, typically 500 nm for visible light. This separation allows evanescent waves 91 from target 82 to be coupled into the aplanatic lens, converting evanescent waves 91 into propagating waves within lens 85. Propagating waves within lens 85 then exit through the spherical surface of the aplanatic lens with a numerical aperture <1, i.e., as propagating waves 92. These waves 92, in turn, are measured by detector 87 in system 100, which may comprise a conventional optical system, e.g., with a CCD. The conventional part of optical system 100 can be, for instance, an optical microscope, whose acceptance NA matches that of the exit NA of aplanatic lens 85, or it can, for instance, be a sub-system of a microscope, so that aplanatic lens 85 may be an integral part of a complete microscope system.

In an example embodiment, system 100 may be configured to increase the information content received from target 82 to reduce the target pitch and/or size (targets 82 may comprise e.g., double, quadruple, and in general multiple patterned gratings) and to enhance system performance directly or indirectly, as is explained below (e.g. reduction of Tool Induced Shift (TIS), cost reduction due to the less stringent requirement on a lower NA objective that can be used instead of currently used objectives, or any other kind of performance enhancement that may be manifested in, but not limited to TIS, precision, accuracy and matching).

Comparing hemispherical lens 85A with Amici lens 85B yields the following differences, which may be utilized in different embodiments of system 100. With n as the refractive index of the aplanatic lens, $NA_{obj}$ as the numerical aperture of the optics following the aplanatic lens, and r as the radius of curvature of the aplanatic lens (see e.g., FIG. 3C). The total numerical aperture in the target space $NA_{total}$ is $n \cdot NA_{obj}$ for hemispherical lens 85A. The total numerical aperture in the target space $NA_{total}$ for Amici lens 85B is $n^2 \cdot NA_{obj}$ for $NA_{obj} < 1/n$, and n for $NA_{obj} > 1/n$. The minimum working distance required for the optics (e.g., illumination arm 86 and collection arm 87, beam splitter 88, and objective lens 89) following the aplanatic lens $WD_{obj}$ is r for hemispherical lens 85A, and $(n+1) \cdot r$ for Amici lens 85B.

Hence, advantageously hemispherical lens 85A has no chromatic aberrations and a shorter working distance $WD_{obj}$, while Amici lens 85B can use lower NA of the objective or optics following the aplanatic lens.

In some example embodiments, the optical material for the aplanatic lens is selected to have as high a refractive index as possible to achieve a high total NA ($NA_{total}$, limited by n). Optical glasses reach values of n≤2, with the refractive index usually increasing towards shorter wavelengths due to dispersion. Crystalline optical materials may have higher refractive indexes, such as rutile ($TiO_2$), with n=2.584 at wavelength of 633 nm. With crystalline materials, the orientation of the crystal and its effect on the optical performance (especially polarization) needs to be taken into account. In some example embodiments, illumination polarization may be manipulated to further improve the optical performance of system 100, as is explained below. Non-limiting examples for materials with a broad spectral passband (transmissive at the required wavelengths) may comprise sapphire, with a relatively high refractive index of 1.77, glasses having a refractive index of 2 (e.g., S-LAH79 from OHARA Corporation), cubic zirconia which is a crystal of refractive index of 2.2, and so forth. The optics following the aplanatic lens (e.g., illumination arm 86 and collection arm 87, beam splitter 88, objective lens 89) may be either refractive, reflective, or catadioptric. The last two alternatives are especially suitable for use at UV-wavelengths.

In some example embodiments, metrology system 100 comprises solid immersion lens 85 as optical element 110, which is arranged to enhance a range of incident angles of radiation on target 82, to enhance the at least first diffraction order measured by the system.

In spectroscopic scatterometry for measurement of both OVL and CD, the sensitivity is expected to be dependent upon the incident angle of the illumination. Using, for example, the configuration in FIG. 3B enables measurement at effectively complex angles (NA>1). Solid immersion lens 85 effectively increases the NA of system 100 to enhance its sensitivity and thus the performance of the spectroscopic based measurement.

In angle-resolved scatterometry there are two main types of measurement: zeroth order, used for grating over grating OVL measurements, ellipsometry and CD measurements; and first order, used for grating over grating OVL measurements. In embodiments, metrology system 100, comprising solid immersion lens 85 as optical element 110, is arranged to enhance the sensitivity of zeroth order measurements. For first order types of measurement, increasing the NA enables the first order to be in the pupil at larger NAs. This effectively enables smaller pitches with the same illumination wavelengths. Also, this enables better separation of the first orders from the zeroth order which decreases the crosstalk between them and increases performance. Hence, some example embodiments of metrology system 100 may be arranged to enhance a range of incident angles of radiation on target 82 to enhance the at least first diffraction order measured by the system.

In some example embodiments, system 100 may further comprise a polarizer (not shown) arranged to control a polarization of the illuminating radiation. The polarizer may comprise a wave plate, or implement any other means of spatial and temporal polarization control. Arranging system 100 to use the polarization content in conjunction with solid immersion enhances NA and may yield extensive advantages in sensitivity and performance. Being a simple addition to the objective, the solid immersion technology allows the usage of all regular optical elements in the optical path such as (but not limited to): a polarizer, analyzer, quasi cross polarization, beam splitter, and beam monitor.

System Advantages and Configuration for Scatterometry Overlay (SCOL) Metrology

Advantageously, system 100 using optical element 110 that provides a higher NA, improves scatterometry overlay (SCOL) metrology in the following aspects. Further, system 100 and optical element 110 may be configured to enhance any of the following advantages.

First, system 100 provides a fundamental performance enhancement involved in the ability to probe smaller values of the pitch and being closer to design rule (DR).

Second, system 100 allows more flexibility to choose wavelengths and pitches. When using first order angle-resolved scatterometry, the use of higher NA enables reduction of target pitch or increase of measurement wavelength, while maintaining the first order within the measurement pupil.

Third, system 100 reduces inaccuracies related to target size and to target noise. The inaccuracies are reduced due to multiple aspects improved by the system. First, for a given cell size, the inaccuracy due to the present mixing of the orders in the pupil becomes smaller since the different orders are further away from each other. Second, it is possible to apodize the first order illumination without a heavy penalty on the SNR (signal to noise ratio). This reduces the tails of the illumination spot which is highly desirable. Third, increasing the illumination NA in system 100 makes the spot size smaller and so also reduces the cell-to-cell contamination.

Additionally, target noise is smaller because when scan area (e.g., target 82) is much larger than the spot size, the inaccuracy related to target-noise becomes proportional to the ratio spot-size/scan-size (if it is a phase noise) or to the ratio correlation-length/scan-size (if it is an amplitude noise). By increasing the illumination NA, system 100 further reduces target noise as the spot-size decreases with increasing illumination NA and as the correlation length decreases with pitch and system 100 can be operated at smaller pitch when illumination NA is higher.

Another advantage of system 100 includes cancelling some of the inaccuracy related to cell-to-cell contamination when system 100 averages over pupil points. In such cases, system 100 may be arranged to have all the +1/−1 orders inside the collection NA, which is easily achievable using optical element 110 such as solid immersion lens 85. Furthermore, system 100 enables the normalization of the 4-cell signal to be performed without the challenge of handling diffraction effects of the illumination non-uniformity on the CFS (Coherent Fourier scatterometry). System 100 may thus use less tight illumination uniformity requirements at illumination arm 86. Also, fixing the pixel size and increasing the NA yields a gain in sensitivity since system 100 actually collects more metrological data.

System Advantages and Configuration for Critical Dimension (CD) Metrology

Advantageously, embodiments of system 100 using optical element 110 that provides a higher NA improves critical dimension (CD) in the following aspects. System 100 and optical element 110 may be configured to enhance any of the following advantages.

First, the larger illumination NA generates a smaller spot on wafer 80, which enables measurement of smaller targets 82.

Second, the larger illumination NA enables the illumination and collection of evanescent waves 91 (see further details below), that is, NA>1, which are of special interest in CD and focus and dose measurements.

Third, measurements by system 100 may be coupled with special illumination and collection polarizations to counter a systematic error caused by total reflection ("total reflection" DC), originating from the planar part of solid immersion hemisphere 85. For example, system 100 may further comprise radial and tangential retarders or polarizers or other retarders or variable or constant polarizers (not shown), which are placed in illumination and collection paths to improve the sensitivity/signal ratio. Of course, a variety of illumination and collection polarizations (either constant or systematic (e.g., radial and tangential) or per pixel (e.g., any pixel of the polarizer/illumination retarder/analyzer/collection retarder has its own properties either constant or adjustable) may be used to improve the measurements on themselves without any other part of the current invention. System 100 may thus be designed to have a much higher sensitivity to signal ratios by incorporating such additional optical elements. Such illumination/collection path enhancements can be used in different metrology systems, e.g., goniometry (angle-resolved scatterometry) and spectrometry (for example, using different objectives for illumination and collection).

For example, simulations of different optical paths for goniometric optical systems with a constant polarizer as analyzer, yield the following results: (i) addition of solid immersion objective 85 placed 10 nm from wafer 80 yields a nine fold improvement in precision; (ii) addition of solid immersion objective 85 placed 50 nm from wafer 80 yields a fourfold improvement in precision; (iii) addition of solid immersion objective 85 placed 100 nm from wafer 80 yields an almost threefold improvement in precision; and, (iv) addition of a fractional (e.g., quarter) waveplate (constant retarder) in the optical path yields a twofold improvement in precision. System 100 with solid immersion lens 85 as optical element 110 is also easier to improve by addition of retarders than a system without optical element 110.

Moiré-Element

In some example embodiments, system 100 may comprise a Moiré-grating or a Moiré-lens as optical element 110 to enhance a spatial resolution of system 100.

The Moiré-element (i.e., grating or lens) may be used to provide a far-field imaging of small pitch target (unresolved pitch) by converting evanescent waves 91 containing information of target position to propagating waves 92. Since the evanescent modes decay on the scale of about a hundred nanometers from target 82, this approach implies placing the Moiré-element as a part of optical element 110 positioned directly in the target near-field. Optical element 110 thus may comprise a grating having a pitch that is close but not equal to the pitch of the measured target 82 ($P_{target}$). After scattering of the light reflected from target 82 on the near-field grating, new diffraction orders corresponding to a coarse pitch, namely:

$$P'_{Moiré} = abs\left(\frac{1}{\frac{1}{P_{target}} - \frac{1}{P_{device}}}\right)$$

are originated which can be propagating waves with a proper choice of the device grating pitch, $P_{device}$.

The Moiré-approach can be applied considering additional gratings in illumination path 86 or in collection path 87 (or actually in both since optical device 110 is located in the target near-field). With additional gratings in illumination path 86, system 100 may comprise a near-field illuminator that provides a Moiré-pattern on target 82 and the light reflected from target 82 contains diffraction orders corresponding to the Moiré-pitch $P_{Moiré}$ which are propagating waves comprising information on target position. With additional gratings in collection path 87, system 100 may comprise a near-field collector which collects the propagating waves corresponding to the Moiré-pitch $P_{Moiré}$ originated after scattering of the light reflected from target 82 on near-field grating that is part of the near-field collector.

In both cases, the main problem is the small amplitude of the diffraction orders compared to the zero order and any type of back scattered light in optical system (ghost images, etc.). For example, even when near field optical device 110 is located at a distance of about 50 nm from target 82, and the pitch of measured target is about 70-80 nm, the amplitude of evanescent mode is reduced by two orders of magnitude. Accordingly, to make this sub resolution imaging possible, it would be desirable to enhance the amplitudes of evanescent modes by system 100 by at least two orders of magnitude.

Optical element 110 may comprise only one or more Moiré-gratings/lenses, a combination of the Moiré-grating/lens and solid immersion lens 85, or a combination of a cascade of Moiré-gratings/lenses and solid immersion lens 85. Either, or both, Moiré-gratings/lenses and solid immersion lens 85 may be used to transform evanescent modes 91 into propagating modes to increase the information content of the first diffraction orders in e.g., imaging OVL and first order SCOL carried out with respect to targets 82 having small pitches. In particular, a combination of solid immersion lens 85 and the Moiré-element may allow an expansion of the range of measurable target. Thus, using solid immersion lens 85 overcomes the limitation of present usage of Moiré-elements, namely their relatively narrow range of measured targets (the range of allowable pitches $P_t$ must satisfy the condition that $1/P_t$ is within $<1/P\pm 2NA/\lambda$ with P being the pitch of the Moiré-element). The same consideration illustrates the advantage of using solid immersion lens 85 with a cascade of Moiré-gratings or lenses.

Dielectric-Metal-Dielectric Stack

Figure 4A:
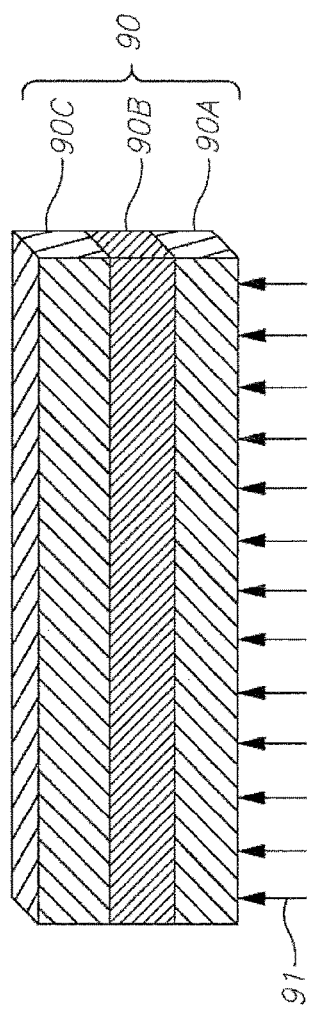
FIG. 4A is a schematic illustration of a dielectric-metal-dielectric stack according to the prior art.

In some example embodiments, metamaterials may also be used to enhance evanescent modes 91 of radiation scattered by target 82. In general, metamaterials are artificial materials with both negative permittivity ($\varepsilon<0$) and negative permeability ($\mu<0$), which provide enhancement of any evanescent mode in a standard material. Moreover, since the behavior of strongly evanescent transverse-electric (TE) wave is ruled mostly by permeability $\mu$ whereas the behavior of strongly evanescent transverse-magnetic (TM) wave is ruled mostly by permittivity $\varepsilon$, optical element 110 may be designed to have only one of $\varepsilon$, $\mu$ negative to enhance only one of the modes. For TM waves, negative permittivity may be sufficient for the required enhancement, and hence optical element 110 may use a proper metal (silver, gold, copper, etc.) which has $\varepsilon<0$ as a true meta-material to enhance evanescent waves. The commonly used configuration for this purpose is a sandwich-like configuration consisting of two dielectric layers (having permittivities $\varepsilon_D$) and metal layer (having permittivity $\varepsilon_M$) with $\varepsilon_M \sim -\varepsilon_D$. FIG. 4A is a schematic illustration of such dielectric-metal-dielectric stack 90 according to the prior art. Evanescent modes 91 may be TM waves for the illustrated case.

In some example embodiments, optical element 100 may comprise dielectric-metal-dielectric stack 90 arranged to enhance evanescent modes 91 of radiation scattered by target 82. A metamaterial, such as dielectric-metal-dielectric stack 90, may be used to increase the sensitivity system 100 to smaller pitches. Such metamaterials may be configured to further enhance evanescent modes 91 based on excitation of surface plasmon modes at interfaces between metal film layer 90B set between dielectric film layers 90A, 90C.

The matching condition, as explained in the following, may be used to calculate the amplitude enhancement of evanescent modes 91, without wishing to be bound by theory. Considering TM wave propagation through film stack 90, comprising metal film 90B surrounded by dielectric films 90A, 90C, the transmission and reflection coefficients may be calculated as following. Denoting the transversal wave number as $q=2\pi/P_{target}$ the wave numbers in the normal direction for each one of the layers I is:

$$k_i = \sqrt{q^2 - \varepsilon_i \left(\frac{\omega}{c}\right)^2}.$$

Evanescent mode amplitude enhancement may take place by the evanescent modes being associated with surface plasmon resonance interactions and it strongly depends on the metal layer thickness. Evanescent mode amplitude enhancement may further be associated with metamaterial properties and can be realized in a wider range of metal layer thickness values. It requires a good matching between parameters of metal and dielectric layers. A good matching is indicated by a matching condition (MC) that approaches zero:

$$MC = 1 + \frac{k_2 \varepsilon_1}{k_1 \varepsilon_2} \Rightarrow 0.$$

Both mechanisms are limited by metal loss coefficient Im($\varepsilon_2$) (i.e., the imaginary part of the permittivity). For silver, which has the smallest losses in visible spectrum range Im($\varepsilon_2$)~0.02, the best amplitude enhancement in layer 90B is about 50. However, when the amplitude decay in the surrounding dielectric layers 90A, 90C and the light reflection between dielectric layers 90A, 90C and air are taken into account, no real enhancement of evanescent modes is achieved by prior art stack 90 that is illustrated in FIG. 4A.

However, modifying the orientation and/or form of stack 90 may in some cases yield a significant overall enhancement of evanescent modes. For example, metrology system 100 may comprise optical element 110 having an inclined dielectric-metal-dielectric stack 90 arranged to enhance evanescent modes of radiation 91 scattered by target 82.

Figure 4B:
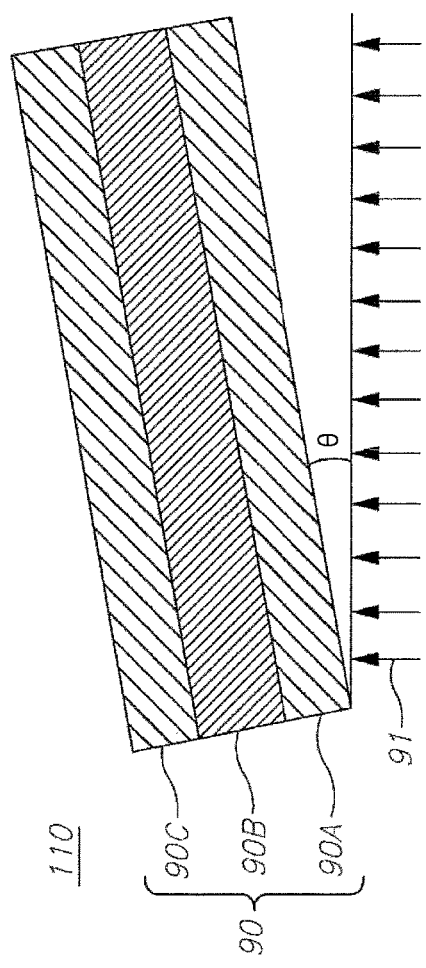
FIG. 4B illustrates an optical element comprising an inclined dielectric-metal-dielectric stack, according to some embodiments of the invention.

FIG. 4B illustrates optical element 110 comprising an inclined dielectric-metal-dielectric stack 90, according to some embodiments of the invention. Inclined dielectric-metal-dielectric stack 90 is positioned at angle θ with respect to target 82. Without wishing to be bound by theory, in the illustrated case, the wave number in the normal direction may be expressed as $k_i = \sqrt{(q\cos\theta + ik_1\sin\theta)^2 - \varepsilon_i k_0^2}$. The matching condition may be expressed as:

$$MC = 1 + \frac{\varepsilon_1 \sqrt{(q\cos\theta + ik_1\sin\theta)^2 - \varepsilon_2 k_0^2}}{\varepsilon_2 \sqrt{(q\cos\theta + ik_1\sin\theta)^2 - \varepsilon_2 k_0^2}} \Rightarrow 0.$$

Using $q^2 \gg |\varepsilon_2| k_0^2$, MC may be approximated by:

$$MC \cong MC_0 - 2i\theta \frac{\varepsilon_1 k_0^2}{q^2}$$

where $MC_0$ is the value of the matching condition without tilt. As a result of the derivation, optical element 110 may be designed to achieve a perfect matching of the imaginary part of MC by adjusting tilt angle θ, and matching the real part of MC by selecting the materials properly. Properly choosing the materials and tilt angle enables the amplitude enhancement to increase up to four orders of magnitude.

In an example embodiment, optical element 110, which comprises periodic dielectric-metal-dielectric stack 90 having undulating surface 96 rising and falling with respect to objective lens 89 and target 82, also enhances evanescent modes of radiation scattered by target 82.

Figure 4C:
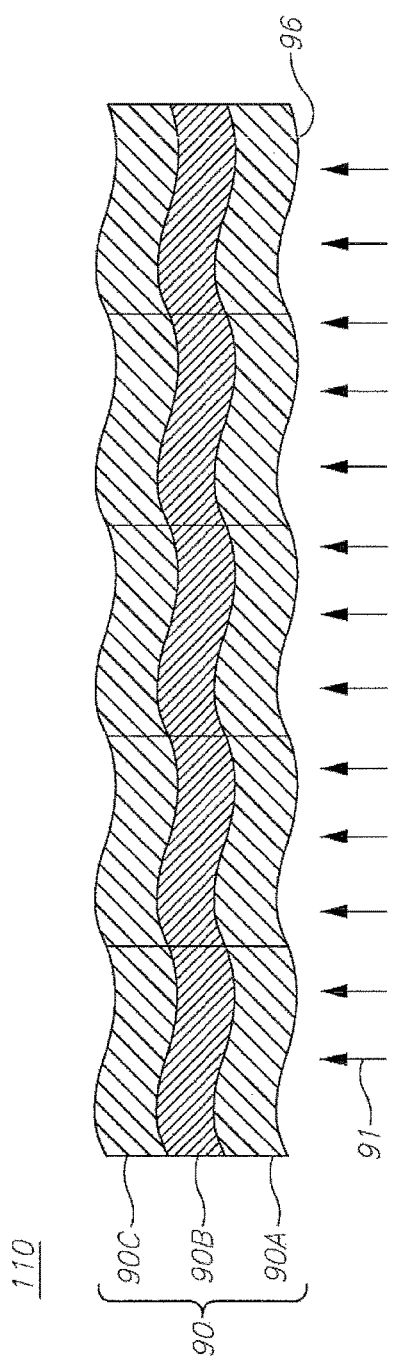
FIG. 4C illustrates an optical element comprising a periodic dielectric-metal-dielectric stack, according to some embodiments of the invention.

FIG. 4C illustrates optical element 110 comprising periodic dielectric-metal-dielectric stack 90, according to some embodiments of the invention. Periodic dielectric-metal-dielectric stack 90 may have sinusoidal surface 96 with respect to target 82. Without wishing to be bound by theory, in the illustrated case, the following expression for the matching condition may be used as a non-limiting example for a simple case in which the periodic function is a pure sine with pitch $P_{device}$ and amplitude A:

$$MC \cong MC_0 - \frac{4\pi A}{P_{device}} i\cos\left(\frac{2\pi}{P_{device}}x\right)\frac{\varepsilon_1 k_0^2}{q^2} \text{sign}(q).$$

In some example embodiments, the surface amplitude A may be chosen to yield a periodic net of points where diffraction orders corresponding to the light reflected from target 82 are enhanced by several orders of magnitude, in which appears the Moiré-pattern with propagating pitch:

$$P_{Moir\acute{e}} = \text{abs}\left(\frac{1}{\frac{1}{P_{target}} - \frac{1}{P_{device}}}\right).$$

Figure 4D:
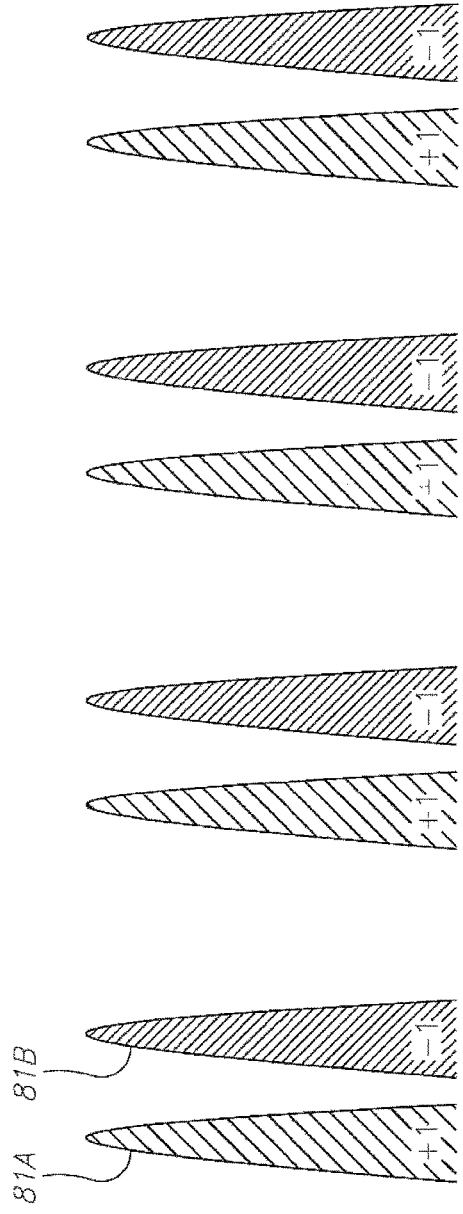
FIG. 4D is a high level schematic illustration of a periodic pattern generated by an optical element, according to some embodiments of the invention.

FIG. 4D is a high level schematic illustration of such a pattern, with amplitudes of the first diffraction orders indicated as "+1" 81A and "−1" 81B, according to some embodiments of the invention.

The following derivation illustrates the efficiency of periodic dielectric-metal-dielectric stack 90 in enhancing evanescent modes of radiation scattered from the target. The following also illustrates the derivation of the conditions presented above, without limiting their applicability.

For inclined stack 90 illustrated in FIG. 4B, assuming a thickness h of the metal layer 90B, an inclination angle θ and the z' axis normal to stack 90 and starting at the lower metal dielectric interface (90A-90C), the electric and magnetic fields can be described as shown below.

In dielectric 90C:

$$\vec{E}_1 = (E_{3x}, 0, E_{3z}) \cdot e^{-(k_1\cos\theta + iq\sin\theta)z'} \cdot e^{(iq\cos\theta - k_1\sin\theta)x' - i\omega t}; \text{ and,}$$

$$\vec{H}_1 = (0, H_{1y}, 0) \cdot e^{-(k_1\cos\theta + iq\sin\theta)z'} \cdot e^{(iq\cos\theta - k_1\sin\theta)x' - i\omega t}.$$

In metal 90B:

$$\vec{E}_2 = (E_{2x}{}^1 e^{-k_2 z'} + E_{2x}{}^2 e^{k_2 z'}, 0, E_{2z}{}^1 e^{-k_2 z'} + E_{2z}{}^2 e^{k_2 z'}) \cdot e^{(iq\cos\theta - k_2\sin\theta)x' - i\omega t};$$

and, $$\vec{H}_2 = (0, H_{2y}{}^1 e^{-k_2 z'} + H_{2y}{}^2 e^{k_2 z'}, 0) \cdot e^{(iq\cos\theta - k_2\sin\theta)x' - i\omega t}.$$

In dielectric 90A:

$$\vec{E}_1 = (E_{1x}{}^1 e^{-(k_1\cos\theta + iq\sin\theta)z'} + E_{1x}{}^2 e^{(k_1\cos\theta + iq\sin\theta)z'}, 0,$$
$$E_{1z}{}^1 e^{-(k_1\cos\theta + iq\sin\theta)z'} +$$
$$E_{1z}{}^2 e^{(k_1\cos\theta + iq\sin\theta)z'}) \cdot e^{(iq\cos\theta - k_1\sin\theta)x' - i\omega t}; \text{ and,}$$

$$\vec{H}_1 = (0, H_{1y}{}^1 e^{-(k_1\cos\theta + iq\sin\theta)z'} + H_{1y}{}^2 e^{(k_1\cos\theta + iq\sin\theta)z'},$$
$$0) \cdot e^{(iq\cos\theta - k_1\sin\theta)x' - i\omega t};$$

where:

$$k_1 = \sqrt{q^2 - \varepsilon_1 \left(\frac{\omega}{c}\right)^2};$$

and, $$k_2 = \sqrt{(q\cos\theta + ik_1\sin\theta)^2 - \varepsilon_2 k_0^2}.$$

When stack 90 is not inclined (FIG. 4A), the transmission coefficient is expressed as:

$$T = -\frac{4\dfrac{\varepsilon_1\sqrt{q^2-\varepsilon_2\left(\frac{\omega}{c}\right)^2}}{\varepsilon_2\sqrt{q^2-\varepsilon_1\left(\frac{\omega}{c}\right)^2}}e^{h\sqrt{q^2-\varepsilon_2\left(\frac{\omega}{c}\right)^2}}}{\left(1-\dfrac{\varepsilon_1\sqrt{q^2-\varepsilon_2\left(\frac{\omega}{c}\right)^2}}{\varepsilon_2\sqrt{q^2-\varepsilon_1\left(\frac{\omega}{c}\right)^2}}\right)^2 - \left(1+\dfrac{\varepsilon_1\sqrt{q^2-\varepsilon_2\left(\frac{\omega}{c}\right)^2}}{\varepsilon_2\sqrt{q^2-\varepsilon_1\left(\frac{\omega}{c}\right)^2}}\right)^2 e^{2h\sqrt{q^2-\varepsilon_2\left(\frac{\omega}{c}\right)^2}}}.$$

And the optimal magnification corresponds to:

$$\min\left\{1 + \frac{\varepsilon_1\sqrt{q^2 - \varepsilon_2 k_0^2}}{\varepsilon_2\sqrt{q^2 - \varepsilon_1 k_0^2}}\right\}$$

where $$k_0 = 2\pi/\lambda.$$

In the case of inclined stack 90 (FIG. 4B), the corresponding condition is:

$$MC = 1 + \frac{\varepsilon_1\sqrt{(q\cos\theta + ik_1\sin\theta)^2 - \varepsilon_2 k_0^2}}{\varepsilon_2\sqrt{(q\cos\theta + ik_1\sin\theta)^2 - \varepsilon_1 k_0^2}} \Rightarrow 0.$$

Assuming θ to be small, the permittivities may be expressed as $\varepsilon_2 = -\varepsilon_1 + \alpha + i\beta$ where both α and β are small, $q^2 \gg |\varepsilon_2|k_0^2$, and using the leading order:

$$MC \cong 1 + \frac{\varepsilon_1\sqrt{(q\cos\theta + ik_1\sin\theta)^2 - \varepsilon_2 k_0^2}}{\varepsilon_2\sqrt{(q\cos\theta + ik_1\sin\theta)^2 - \varepsilon_1 k_0^2}}$$

$$\cong 1 + \frac{\varepsilon_1\sqrt{(1+i\theta)^2 - \varepsilon_2 k_0^2/q^2}}{\varepsilon_2\sqrt{(1+i\theta)^2 - \varepsilon_1 k_0^2/q^2}}$$

$$\cong \frac{\varepsilon_1 k_0^2}{q^2(1+i\theta)^2} + \frac{\alpha + i\beta}{\varepsilon_1}$$

$$\cong \frac{\varepsilon_1 k_0^2}{q^2} + \frac{\alpha + i\beta}{\varepsilon_1} - 2i\theta\frac{\varepsilon_1 k_0^2}{q^2}.$$

The maximum magnification may be achieved when:

$$\alpha \cong -[\text{Re}(\varepsilon_1)]^2 \frac{k_0^2}{q^2};$$

and, $$\beta \cong -2\text{Re}(\varepsilon_1)\cdot\text{Im}(\varepsilon_1)\frac{k_0^2}{q^2} + 2i\theta[\text{Re}(\varepsilon_1)]^2\frac{k_0^2}{q^2}.$$

With these equations, it is possible to design optical element 110 to achieve the perfect matching of the imaginary part of MC by configuring inclination angle θ, and matching the real part of MC by properly selecting the materials (metal and dielectrics).

In order to achieve separation of the +1 and −1 orders of diffraction, the inclination principle illustrated in FIG. 4B must be applied repeatedly with inclinations to both sides. Such a configuration is a periodic undulating configuration of stack 90 illustrated in FIG. 4C. In a non-limiting example, periodically undulating surfaces may be expressed as a cosine, for example in region 90C:

$$\vec{E}_1 = \left(E^1_{1x'}e^{-[k_1 + iq\frac{2\pi a}{P}\cos(\frac{2\pi}{P}x)]z} + E^2_{1x'}e^{[k_1 + iq\frac{2\pi a}{P}\cos(\frac{2\pi}{P}x)]z}, 0,\right.$$
$$\left. E^1_{1z'}e^{-[k_1 + iq\frac{2\pi a}{P}\cos(\frac{2\pi}{P}x)]z} + E^2_{1z'}e^{[k_1 + iq\frac{2\pi a}{P}\cos(\frac{2\pi}{P}x)]z}\right)\cdot e^{[iq - k_1\frac{2\pi a}{P}\cos(\frac{2\pi}{P}x)]x - i\omega t};$$

and, $$\vec{H}_1 = \left(0, H^1_{1y}e^{-[k_1 + iq\frac{2\pi a}{P}\cos(\frac{2\pi}{P}x)]z} + H^2_{1y}e^{[k_1 + iq\frac{2\pi a}{P}\cos(\frac{2\pi}{P}x)]z}, ,0\right)\cdot$$
$$e^{[iq - k_1\frac{2\pi a}{P}\cos(\frac{2\pi}{P}x)]x - i\omega t}.$$

And the resulting matching coefficient is:

$$MC \cong \frac{\varepsilon_1 k_0^2}{q^2} + \frac{\alpha + i\beta}{\varepsilon_1} - \frac{4\pi a}{P}i\cos\left(\frac{2\pi}{P}x\right)\frac{\varepsilon_1 k_0^2}{q^2}\text{sign}(q).$$

Hence, the pitch of periodic stack 90 may be adapted to yield the required separation of the +1 and −1 orders of diffraction, schematically illustrated in FIG. 4D.

Resonating Illuminating Optical Element

As dielectric layers 90A, 90C are preferably thin in order not to eliminate the amplitude enhancement produced by metal layer 90B, the matching condition between dielectric layers 90A, 90C and surrounding medium may destroy the enhancement capability of a device as a whole. However, damping of the amplitude enhancement by the interface between dielectric layers 90A, 90C and the surrounding air may be overcome in the following manner.

Figure 5A:
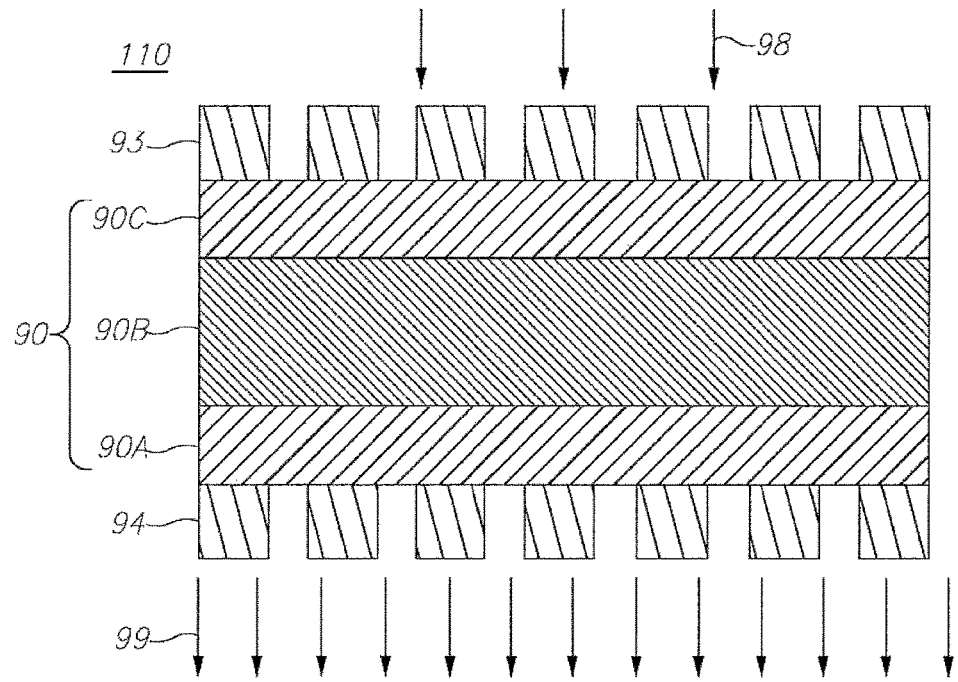
FIG. 5A is a high level schematic illustration of an illuminating optical element, according to some embodiments of the invention.
Figure 5B:
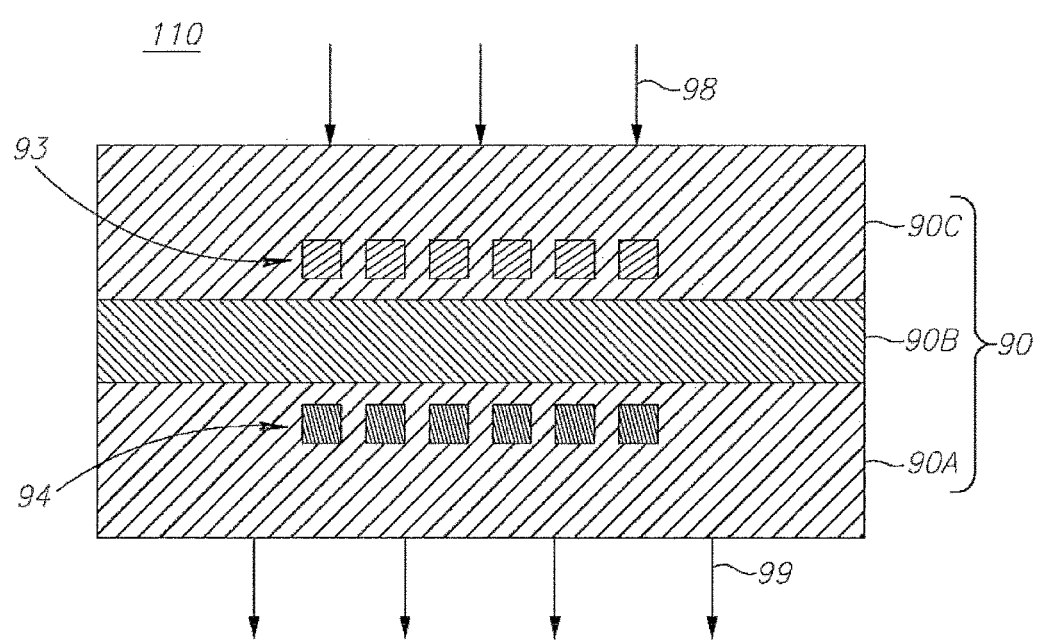
FIG. 5B is a high level schematic illustration of an illuminating optical element, according to some embodiments of the invention.
Figure 6A:
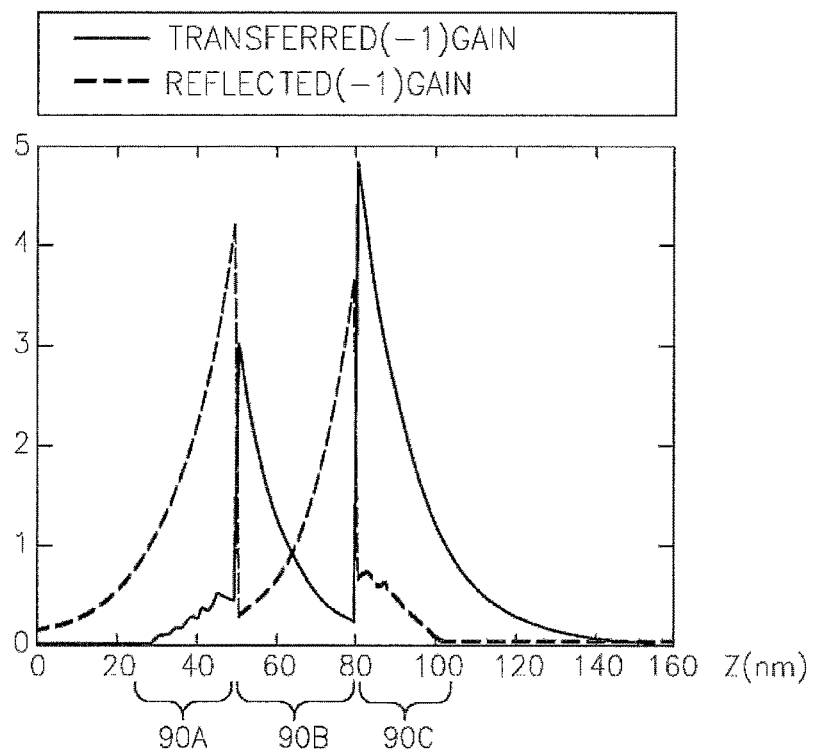
FIG. 6A is a graph that illustrates simulation results of the operation of an illuminating optical element, according to some embodiments of the invention.
Figure 6B:
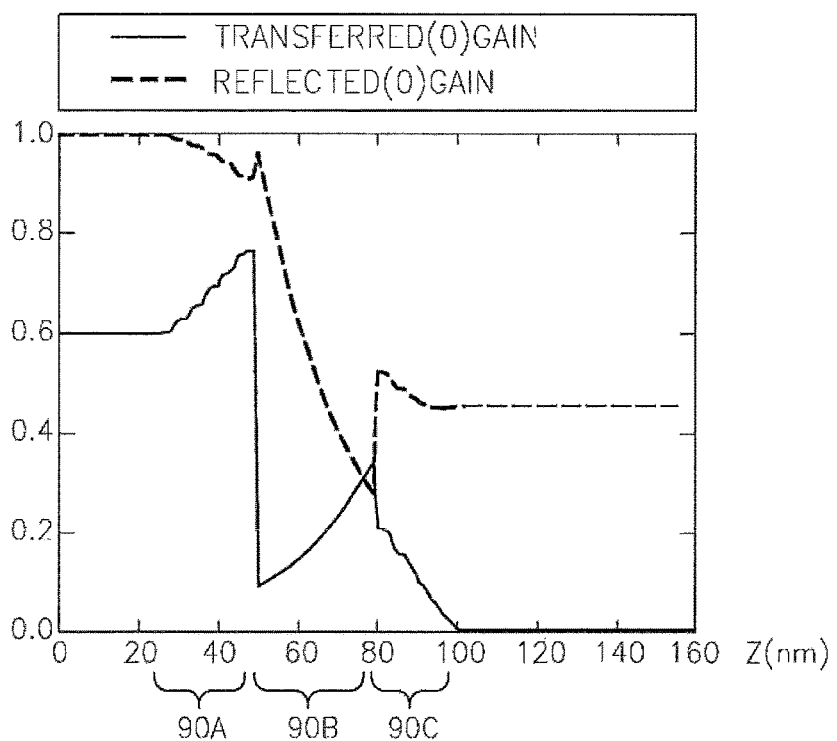
FIG. 6B is a graph that illustrates simulation results of the operation of an illuminating optical element, according to some embodiments of the invention; and, FIG. 7 is a high level schematic flowchart of a metrology method according to some embodiments of the invention.

Considering the Moiré-approach for the illumination path (see above) in more detail, it is noted that the purpose of near field device in illumination path is to create the periodic illumination with a pitch close to the pitch of measured target. A significant improvement may be achieved by placing two gratings in the near field of illuminating optical element 110. An additional purpose is to enhance the amplitude of the incident light by at least two orders of magnitude. These purposes may be fulfilled using optical elements 110 illustrated e.g., in FIGS. 5A and 5B. FIGS. 5A and 5B are a high level schematic illustration of illuminating optical element 110, according to some embodiments of the invention; and FIGS. 6A and 6B are graphs that illustrate simulation results of the operation of illuminating optical element 110, according to some embodiments of the invention.

Generally, this design is to scatter illuminating light 98 before it reaches target 82. This means that target 82 is illuminated with a known diffraction pattern. Scattering device 110 enhances the ±1 diffraction orders, when using the right pitch to scatter those orders, once they reach the target most of their energy would transform into the zero order scattered from the target which is a propagating wave.

In some example embodiments, metrology system 100 may comprise optical element 110 having dielectric-metal-dielectric stack 90 (with layers 90A, 90B, 90C matched according to the matching condition, as explained above) associated with two gratings 93, 94. FIG. 5A illustrates an example embodiment with stack 90 enclosed within gratings 93, 94, and FIG. 5B illustrates an embodiment with gratings 93, 94 being embedded in dielectric layers 90C, 90A (respectively) of stack 90.

In some example embodiments, the permittivity ($\varepsilon$) of gratings 93, 94 is a free parameter that can be altered to gain more reflection or transmission as needed. The thickness of dielectric layers 90A, 90C may be selected to balance degradation of signal intensity by too thick layers and attenuation of the enhancement effect by a too close air-dielectric interface (the active amplification area must be sufficiently isolated from the air surrounding it the dielectrics). The thickness of metal layer 90B may also be selected to balance between increasing the gain of the evanescent modes enhancement and losses to the scattered zero order returning from target 82 which carries the information (after being converted from the illuminated amplified evanescent modes).

Dielectric-metal-dielectric stack 90 may be arranged to amplify evanescent modes 99 of radiation 98 illuminating target 82. In some example embodiments, gratings 93, 94 have the same pitch and act as resonators for evanescent modes being repeatedly amplified in metal layer 90B. In some example embodiments, and without wishing to be bound by theory, resonating optical element 110 may operate as an amplifying resonance cavity of evanescent modes. In some example embodiments, the matching condition may be selected in a manner similar to the described above. The matching condition sets the permittivity ($\varepsilon$) of the metal and dielectric, while permittivity ($\varepsilon$) of gratings 93, 94 and their form are free parameters and can be altered to gain more reflection or transmission as needed.

Without wishing to be bound by theory, the area between gratings 93, 94 can be thought of as an interferometer, in which the light that is scattered on first grating 93 creates evanescent modes that are amplified in the ±1 diffraction orders and then transformed back to propagating zero-order once scattered from target 82. These evanescent modes are enhanced inside metal layer 90B as surface plasmons are created alongside the border of the metal (as it is matched with the dielectric and has a negative diffraction index). Once the evanescent modes reach second grating 94, some are scattered and some transmitted forward. The scattered modes transform into zero order and propagate within metal layer 90B (losing some energy inside it) and are being scattered again on upper grating 93 creating the same effect again. The incoherent sum of all the first order modes that pass lower grating 94 is total light intensity 99 that reaches target 82, much like in a Fabry-Perot interferometer.

The parameters that control the gain are the geometry of both gratings 93, 94, the permittivity ($\varepsilon$) of gratings 93, 94 and the distance between gratings 93, 94 to metal layer 90B. These parameters may be configured to set the reflection and transmission factors (see example below). For example, grating 94 may have a large reflection factor letting only a small portion of the light escape the active area between gratings 93, 94, and by doing so enabling the resonant behavior of optical element 110. Since the wave between gratings 93, 94 is propagating, the distance between gratings 93, 94 and metal layer 90B determines the amplitude along the propagating wave cycle which hits gratings 93, 94. Since a propagating wave is sinusoidal in behavior, the distance may be set so that the sinusoidal curve describing the wave reaches its peak at each one of gratings 93, 94. The pitch of optical element 110 is matched to the pitch of target 82, to ensure that the scattered ±1 diffraction modes transforms into propagating zero order mode.

FIGS. 6A and 6B are graphs that illustrate simulation results of the operation of illuminating optical element 110, according to some embodiments of the invention. The results relate to optical element 110 as illustrated in FIG. 5B. FIG. 6A illustrates the gains with respect to the norms of the transferred and reflected −1 order, and FIG. 6B illustrates the gains with respect to the norms of the transferred and reflected 0 order, both after optimization of the grating's $\varepsilon$. FIGS. 6A and 6B illustrate the resonance effect between gratings 93, 94 and the transformation of energy between the modes.

Optical element 110 thus achieves two goals, namely to enhance the evanescent modes and reduce the propagating zero order which may contaminate the information contained in the ±1 modes. Optical element 110 thus also reduces the need for a field stop. The dimensions of layers 90A, 90B, 90C and gratings 93, 94 and their relative positions may be configured to further increase the gain achieved by optical element 110.

Generally speaking, metal layer 90B in the middle of optical element 110 plays a role of an active medium for evanescent modes, whereas gratings 93, 94 on both sides provide a resonance condition allowing to: (1) achieve the maximum enhancement; and, (2) provide the required isolation from the surrounding medium. Such optical elements may be understood as an evanescent-mode laser. It follows from numerical simulations that a given configuration allows the two orders of magnitude enhancement even without fine-tuning of the parameters for any surrounding medium. Some combination of the periodic sandwich configuration where the period, as an example, equals to the double period of two surrounding gratings is also possible.

Optical element 110, while enhancing the evanescent modes, is attenuating propagating modes which include zero order. Therefore, this attenuation could be used as a way to enhance first order modes while suppressing the zero order which may improve performance of measurement.

Since the gratings pitches and modulation depths are an important parameter in the device performance and are somewhat dependent on the target and/or optical parameters (e.g., wavelength), system 100 may advantageously control the grating pitches and modulation depths. This could be achieved by various physical phenomena, including (but not limited to): the photorefractive effect (use of photorefractive material and an illumination beam with the proper spatial properties (e.g., diffraction between two beams which yields a sine pattern) incident upon it with proper power—control of period and modulation depth); the acousto-optic effect; the electro-optic effect; and, a combination of the above.

The use of a gain/active medium (e.g., pumped laser materials) in the intermediate layers might enhance light traversing the said medium and reduce overall losses.

Optical element 110 may be manufactured by conventional methods, e.g., e-beam, lithography (even using segmentation).

Optical element 110 may enhance performance for design rule and non-design rule targets.

Figure 7:
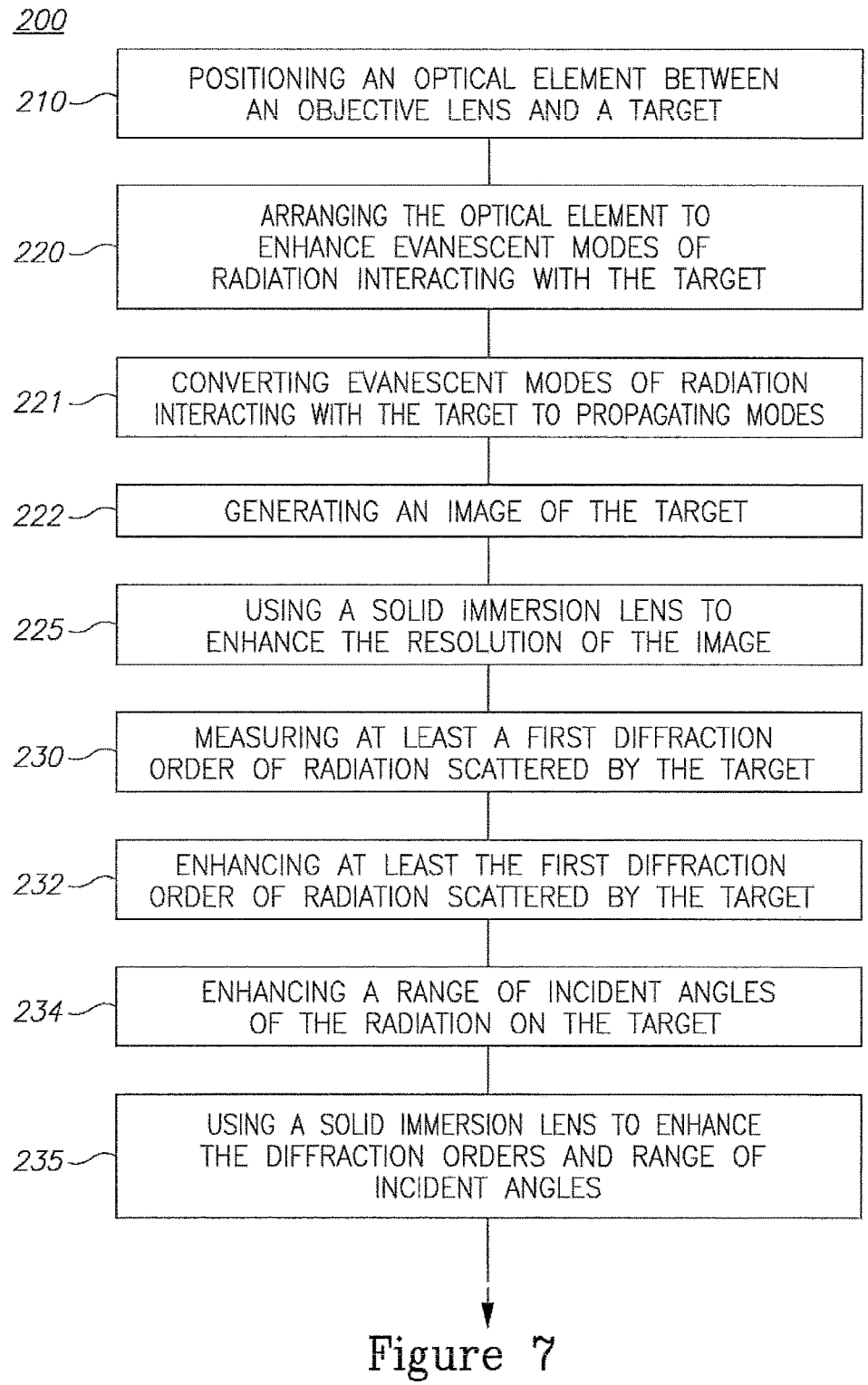

FIG. 7 is a high level schematic flowchart of metrology method 200 according to some embodiments of the invention. Metrology method 200 may comprise the following stages: positioning an optical element between an objective lens and a target (stage 210) and arranging the optical element to enhance evanescent modes of radiation reflected by the target (stage 220). The optical element may be further arranged to convert evanescent modes of radiation interacting with the target to propagating modes (stage 221).

In embodiments, metrology method 200 may comprise generating an image of the target (stage 222) and using a solid immersion lens to enhance a resolution of the image (stage 225).

In embodiments, metrology method 200 may comprise measuring at least a first diffraction order of radiation scattered by the target (stage 230) and enhancing at least the first diffraction order of radiation scattered by the target (stage 232) and/or enhancing a range of incident angles of the radiation on the target (stage 234).

In some example embodiments, metrology method 200 may comprise using a solid immersion lens to enhance the diffraction orders and range incident angles (stage 235).

In some example embodiments, metrology method 200 may comprise enhancing a spatial resolution of scattered radiation (stage 240), e.g., by using a Moiré-grating to enhance the spatial resolution (stage 242) and/or by configuring the optical element to enhance evanescent modes of radiation scattered by the target (stage 250).

In some example embodiments, metrology method 200 may comprise using an inclined dielectric-metal-dielectric stack to enhance the evanescent modes (stage 252), using a periodic dielectric-metal-dielectric stack having an undulating surface to enhance the evanescent modes (stage 254) and/or using a dielectric-metal-dielectric stack associated with two gratings to enhance evanescent modes of radiation scattered by at least one of the gratings (stage 260).

The invention is not limited to those diagrams or to the corresponding descriptions. For example, flow need not move through each illustrated box or state, or in exactly the same order as illustrated and described.

Thus, it is seen that the objects of the present invention are efficiently obtained, although modifications and changes to the invention should be readily apparent to those having ordinary skill in the art, which modifications are intended to be within the spirit and scope of the invention as claimed. It also is understood that the foregoing description is illustrative of the present invention and should not be considered as limiting. Therefore, other embodiments of the present invention are possible without departing from the spirit and scope of the present invention as claimed.

What is claimed is:

1. A metrology system, comprising:
an illumination sub-system configured to illuminate an overlay metrology target with a first evanescent mode of radiation along an illumination optical path;
a collection sub-system configured to measure a second evanescent mode of radiation scattered by the overlay metrology target along a collection optical path, the second evanescent mode of radiation including at least a first diffraction order of radiation;
an objective lens configured to at least one of transmit the first evanescent mode of radiation from the illumination sub-system or transmit the second evanescent mode of radiation scattered by the overlay metrology target to the collection sub-system; and
one or more optical elements including at least a dielectric-metal-dielectric stack,
wherein the dielectric-metal-dielectric stack includes a first dielectric layer, a metal layer disposed on the first dielectric layer, and a second dielectric layer disposed on the metal layer,
wherein the first dielectric layer includes a sinusoidal-shaped top surface, wherein the metal layer includes a sinusoidal-shaped bottom surface that substantially conforms to the sinusoidal-shaped top surface of the first dielectric layer, wherein the metal layer includes a sinusoidal-shaped top surface that substantially conforms to a sinusoidal-shaped bottom surface of the second dielectric layer,
wherein the dielectric-metal-dielectric stack is positioned between the objective lens and the overlay metrology target, wherein the dielectric-metal-dielectric stack is configured to amplify at least one of at least the first evanescent mode of radiation or the second evanescent mode of radiation interacting with the overlay metrology target and configured to inhibit a zeroth-order mode of radiation from contaminating the second evanescent mode of radiation.

2. The metrology system of claim 1, wherein the one or more optical elements are configured to convert at least one of the first evanescent mode of radiation or the second evanescent mode of radiation to a propagating mode of radiation.

3. The metrology system of claim 1, wherein the one or more optical elements include a solid immersion lens configured to amplify a resolution of the metrology system.

4. The metrology system of claim 3, wherein the solid immersion lens illuminates the overlay metrology target with the first evanescent mode of radiation from the illumination sub-system to generate an image of the overlay metrology target.

5. The metrology system of claim 1, wherein the one or more optical elements include a solid immersion lens configured to increase a range of incident angles of radiation on the overlay metrology target, and further configured to amplify the second evanescent mode of radiation including the at least the first diffraction order of radiation.

6. The metrology system of claim 1, wherein the dielectric-metal-dielectric stack is inclined at an angle relative to at least one of the top surface of the overlay metrology target or the bottom surface of the objective lens, wherein the dielectric-metal-dielectric stack is configured to amplify the second evanescent mode of radiation scattered by the overlay metrology target.

7. The metrology system of claim 1, wherein a sinusoidal-shaped bottom surface of the first dielectric layer and a sinusoidal-shaped top surface of the second dielectric layer do not substantially conform to a top surface of the overlay metrology target or a bottom surface of the objective lens, wherein the dielectric-metal-dielectric stack is configured to amplify the second evanescent mode of radiation scattered by the overlay metrology target.

8. A metrology method, comprising:
positioning one or more optical elements including at least a dielectric-metal-dielectric stack between an objective lens and an overlay metrology target, wherein the objective lens is configured to at least one of transmit a first evanescent mode of radiation from an illumination sub-system of a metrology system or transmit a second evanescent mode of radiation scattered by the overlay metrology target to a collection sub-system of the metrology system;

amplifying at least one of at least the first evanescent mode of radiation or the second evanescent mode of radiation interacting with the target via the one or more optical elements including at least the dielectric-metal-dielectric stack;

inhibiting a zeroth-order mode of radiation contaminating a second evanescent mode of radiation scattered by the overlay metrology target via the one or more optical elements including at least the dielectric-metal-dielectric stack; and measuring at least a first diffraction order of radiation in the second evanescent mode of radiation scattered by the overlay metrology target with the collection sub-system, wherein the dielectric-metal-dielectric stack includes a first dielectric layer, a metal layer disposed on the first dielectric layer, and a second dielectric layer disposed on the metal layer, wherein the first dielectric layer includes a sinusoidal-shaped top surface, wherein the metal layer includes a sinusoidal-shaped bottom surface that substantially conforms to the sinusoidal-shaped top surface of the first dielectric layer, wherein the metal layer includes a sinusoidal-shaped top surface that substantially conforms to a sinusoidal-shaped bottom surface of the second dielectric layer, wherein the dielectric-metal-dielectric stack is positioned a selected distance from a top surface of the overlay metrology target and a bottom surface of the objective lens.

9. The method of claim 8, further comprising:
converting at least one of the first evanescent mode of radiation or the second evanescent mode of radiation interacting with the overlay metrology target into a propagating mode of radiation.

10. The metrology method of claim 8, further comprising:
generating an image of the overlay metrology target by using a solid immersion lens as an optical element of the one or more optical elements to illuminate the overlay metrology target with the first evanescent mode of radiation from the illumination sub-system.

11. The metrology method of claim 10, wherein the solid immersion lens is configured to increase a spatial resolution of the metrology system.

12. The metrology method of claim 8, further comprising:
amplifying the second evanescent mode of radiation including the at least the first diffraction order of radiation scattered by the overlay metrology target by using a solid immersion lens as an optical element of the one or more optical elements to increase a range of incident angles of the radiation on the overlay metrology target.

13. The metrology method of claim 8, wherein the dielectric-metal-dielectric stack is inclined at an angle relative at least one of the top surface of the overlay metrology target or the bottom surface of the objective lens.

14. The metrology method of claim 8, wherein a sinusoidal-shaped bottom surface of the first dielectric layer and a sinusoidal-shaped top surface of the second dielectric layer do not substantially conform to a top surface of the overlay metrology target or a bottom surface of the objective lens.

15. A metrology system, comprising:
an illumination sub-system configured to illuminate an overlay metrology target with a first evanescent mode of radiation along an illumination optical path;

a collection sub-system configured to measure a second evanescent mode of radiation scattered by the overlay metrology target along a collection optical path, the second evanescent mode of radiation including at least a first diffraction order of radiation;

an objective lens configured to at least one of transmit the first evanescent mode of radiation from the illumination sub-system or transmit the second evanescent mode of radiation scattered by the overlay metrology target to the collection sub-system; and one or more optical elements including at least a dielectric-metal-dielectric stack, wherein the dielectric-metal-dielectric stack includes a first dielectric layer, a metal layer disposed on the first dielectric layer, and a second dielectric layer disposed on the metal layer, wherein a first diffraction grating is coupled to the first dielectric layer and a second diffraction grating is coupled to the second dielectric layer, wherein the dielectric-metal-dielectric stack is positioned between the objective lens and the overlay metrology target, wherein the dielectric-metal-dielectric stack is positioned a selected distance from a top surface of the overlay metrology target and a bottom surface of the objective lens, wherein the dielectric-metal-dielectric stack is configured to amplify at least one of at least the first evanescent mode of radiation or the second evanescent mode of radiation interacting with the overlay metrology target and configured to inhibit a zeroth-order mode of radiation from contaminating the second evanescent mode of radiation.

16. The system of claim 15, wherein the first diffraction grating is coupled to a bottom surface of the first dielectric layer, wherein the second diffraction grating is coupled to a top surface of the second dielectric layer.

17. The system of claim 15, wherein the first diffraction grating is embedded in the first dielectric layer, wherein the second diffraction grating is embedded in the second dielectric layer.

* * * * *